United States Patent
Moeller et al.

(12)

(10) Patent No.: US 6,770,102 B1
(45) Date of Patent: Aug. 3, 2004

(54) AGENT FOR DYING KERATIN FIBERS

(75) Inventors: Hinrich Moeller, Monheim (DE); Doris Oberkobusch, Duesseldorf (DE); Horst Hoeffkes, Duesseldorf (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 229 days.

(21) Appl. No.: 10/048,208

(22) PCT Filed: Aug. 2, 2000

(86) PCT No.: PCT/EP00/07163

§ 371 (c)(1),
(2), (4) Date: May 3, 2002

(87) PCT Pub. No.: WO01/13866

PCT Pub. Date: Mar. 1, 2001

(30) Foreign Application Priority Data

Aug. 5, 1999 (DE) ......................... 199 36 911

(51) Int. Cl.[7] ................................. A61K 7/13
(52) U.S. Cl. ...................... 8/405; 8/406; 8/407; 8/574; 8/575; 8/576; 8/587; 8/592; 8/607; 8/608
(58) Field of Search ............................ 8/405, 406, 407, 8/574, 575, 576, 587, 592, 607, 608

(56) References Cited

U.S. PATENT DOCUMENTS

| | | | |
|---|---|---|---|
| 4,865,774 A | 9/1989 | Fabry et al. ............... | 252/554 |
| 4,931,218 A | 6/1990 | Schenker et al. .......... | 252/551 |
| 5,034,014 A | 7/1991 | Wenke ....................... | 8/408 |
| 5,279,616 A | 1/1994 | Lang et al. ................. | 8/406 |
| 5,294,726 A | 3/1994 | Behler et al. ............... | 554/98 |
| 6,371,993 B1 * | 4/2002 | Moeller et al. ............ | 8/407 |

FOREIGN PATENT DOCUMENTS

| | | | |
|---|---|---|---|
| DE | 37 23 354 | 1/1989 | |
| DE | 37 25 030 | 2/1989 | |
| DE | 39 26 344 | 2/1991 | |
| DE | 198 20 894 | 11/1999 | |
| EP | 0 502 783 | 9/1992 | |
| EP | 0 820 759 | 1/1998 | |
| FR | 2 787 707 | 6/2000 | |
| FR | 2 787 708 | 6/2000 | |
| WO | WO 99/18916 | * 4/1999 | ............ A61K/7/00 |
| WO | WO 00/33799 | 6/2000 | |

OTHER PUBLICATIONS

The Science of Hair Care, Chapter 7, pp. 235–261, published in vol. 7 of Dermatology, Marcel Dekker Inc. NY/Basle (1986).

The Science of Hair Care, Chapter 8, pp. 263–286, published in vol. of 7 of Dermatology, Marcel Dekker, Inc. NY/Basle (1986).

EU Inventory of Cosmetic Ingredients, Colipa, Mar. 1996—on diskette.

* cited by examiner

*Primary Examiner*—Brian P. Mruk
*Assistant Examiner*—Eisa Elhilo
(74) *Attorney, Agent, or Firm*—Stephen D. Harper; Gregory M. Hill

(57) ABSTRACT

A coloring composition and a method of coloring keratin-containing fibers are provided. The coloring composition contains a mixture of and/or a reaction product of at least one aromatic aldehyde or ketone and at least one CH-active compound. In the method of the present invention, the aromatic aldehyde or ketone and the CH-active compound may be applied to keratin-containing fibers simultaneously or successively.

20 Claims, No Drawings

AGENT FOR DYING KERATIN FIBERS

CROSS REFERENCE TO RELATED APPLICATIONS

This application is a national stage application under 35 U.S.C. §371 of international application PCTIEP00/07163 filed on Aug. 2, 2000, the international application not being published in English. This application also claims priority under 35 U.S.C. §119 to DE 199 36 911.9 filed on Aug. 5, 1999.

BACKGROUND OF THE INVENTION

This invention relates to a composition for coloring keratin fibers, more particularly human hair, which contains a combination of aromatic aldehydes or ketones and CH-active compounds, to the use of this combination as a coloring component in hair colorants and to a process for coloring keratin-containing fibers, more particularly human hair.

In general, keratin-containing fibers, for example hair, wool or pelts, are dyed either with substantive dyes or with oxidation dyes which are formed by oxidative coupling of one or more primary intermediates with one another or with one or more secondary intermediates. Primary and secondary intermediates are also known as oxidation dye precursors.

The primary intermediates normally used are primary aromatic amines containing another free or substituted hydroxy or amino group in the para or ortho position, diaminopyridine derivatives, heterocyclic hydrazones, 4-aminopyrazolone derivatives and 2,4,5,6-tetraaminopyrimidine and derivatives thereof.

Special representatives are, for example, p-phenylenediamine, p-toluylenediamine, 2,4,5,6-tetraaminopyrimidine, p-aminophenol, N,N-bis-(2-hydroxyethyl)p-phenylenediamine, 2-(2,5-diaminophenyl)-ethanol, 2-(2,5-diaminophenoxy)ethanol, 1-phenyl-3-carboxyamido4-amino-5-pyrazolone, 4-amino-3-methylphenol, 2-aminomethyl-4-aminophenol, 2-hydroxymethyl-4-aminophenol, 2-hydroxy-4,5,6-triaminopyrimidine, 2,4-dihydroxy-5,6-diaminopyrimidine and 2,5,6-triamino-4-hydroxypyrimidine.

The secondary intermediates used are generally m-phenylene-diamine derivatives, naphthols, resorcinol and resorcinol derivatives, pyrazolones, m-aminophenols and substituted pyridine derivatives. Particularly suitable secondary intermediates are α-naphthol, 1,5-, 2,7- and 1,7-dihydroxynaphthalene, 5-amino-2-methylphenol, m-aminophenol, resorcinol, resorcinol monomethyl ether, m-phenylenediamine, 2,4-diaminophenoxyethanol, 2-amino-4-(2-hydroxyethylamino)anisole (Lehmann's blue), 1-phenyl-3-methyl-5-pyrazolone, 2,4-dichloro-3-aminophenol, 1,3-bis-(2,4-diaminophenoxy)-propane, 2-chlororesorcinol, 4-chlororesorcinol, 2-chloro-6-methyl-3-aminophenol, 2-methyl resorcinol, 5-methyl resorcinol, 3-amino-6-methoxy-2-methylaminopyridine and 3,5-diamino-2,6-dimethoxypyridine.

With regard to other typical dye components, reference is specifically made to the series entitled "Dermatology" (Editors: Ch. Culnan and H. Maibach), Marcel Dekker Inc., New York/Basel, 1986, Vol. 7, Ch. Zviak, The Science of Hair Care, Chapter 7 (pages 248–250; Substantive Dyes) and Chapter 8 (pages 264–267; OxidaUon Dye Precursors) and to the "Europäische Inventar der Kosmetik-Rohstoffe" published by the European Commission and available on floppy disk from the Bundesver-band Deutscher Industrie- und Handelsunternehmen für Arzneimittel, Reformwaren und Körperpflegemittel e.V., Mannheim, Germany.

Although intensive colors with good fastness properties can be obtained with oxidation dyes, the color is generally developed under the influence of oxidizing agents, such as $H_2O_2$ for example, which in some cases can result in damage to the fibers. In addition, some oxidation dye precursors or certain mixtures of oxidation dye precursors can occasionally have a sensitizing effect in people with sensitive skin. Although substantive dyes are applied under more moderate conditions, their disadvantage is that, in many cases, the colors obtained often have inadequate fastness properties.

The use of the combination of aromatic aldehydes or ketones and CH-active compounds described hereinafter for coloring keratin-containing fibers has not hitherto been known.

The problem addressed by the present invention was to provide colorants for keratin fibers, more especially human hair, which would be at least equivalent in quality to conventional oxidation hair dyes in regard to depth of color, grey coverage and fastness properties, but which would not necessarily have to contain oxidizing agents, such as $H_2O_2$ for example. In addition, the colorants according to the invention would have very little, if any, sensitizing potential.

It has surprisingly been found that the combination of the aromatic aldehydes or ketones represented in formula I and CH-active compounds corresponding to formulae II and/or III is eminently suitable for coloring keratin-containing fibers, even in the absence of oxidizing agents. They give colors with excellent brilliance and depth of color and lead to a wide variety of shades. In principle, however, oxidizing agents may be present.

SUMMARY OF THE INVENTION

The present invention relates to a composition for coloring keratin-containing fibers, more particularly human hair, containing a combination of aromatic aldehydes or ketones corresponding to formula I:

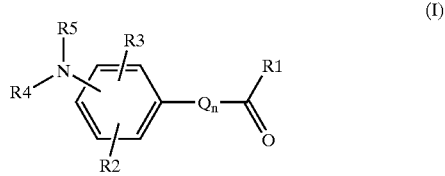

in which $R^1$ is a hydrogen atom, a $C_{1-4}$ alkyl or an aryl group, $R^2$ and $R^3$ independently of one another represent a hydrogen atom, a $C_{1-4}$ alkyl group, a halogen atom, a hydroxy, $C_{1-4}$ alkoxy or nitro group or together form a fused aromatic ring, $R^4$ and $R^5$ represent a hydrogen atom, a $C_{1-4}$ alkyl, $C_{2-4}$ hydroxyalkyl, $C_{1-4}$ alkenyl or aryl group or, together with the nitrogen atom, form a five- to seven-membered heterocyclic ring or one of them forms a saturated or unsaturated 5-, 6- or 7-membered ring with one of the substituents $R^2$ or $R^3$, Q is a direct bond or a vinylene or vinylidene group which, together with one of the two substituents $R^4$ or $R^5$, may form an indole ring or—where an exocyclic double bond is formed—an indoline ring and n=1 or 2, and CH-active compounds corresponding to formulae II and/or III:

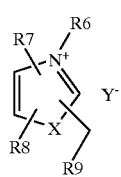
(II)

in which
- $R^6$ is a $C_{1-10}$ alkyl, $C_{2-10}$ alkenyl, $C_{2-4}$ hydroxyalkyl, $C_{2-4}$ carboxyalkyl, $C_{2-4}$ sulfoalkyl or aralkyl group,
- $R^7$ and $R^8$ independently of one another represent a hydrogen atom, a $C_{1-4}$ alkyl group, a halogen atom, a hydroxy, $C_{1-4}$ alkoxy or nitro group or together form a fused aromatic ring,
- $R^9$ represents a hydrogen atom, a $C_{1-4}$ alkyl or an aryl group,
- X is an oxygen or sulfur atom, the group $>N-R^{12}$ or $-CH=CH-$, where $R^{12}$ is a $C_{1-4}$ alkyl, $C_{2-4}$ carboxyalkyl, $C_{2-4}$ sulfoalkyl, $C_{2-4}$ sulfoxyalkyl, $C_{2-4}$ hydroxyalkyl or aralkyl group, and
- $Y^-$ is an anion selected from halide, $C_{1-4}$ alkyl sulfate, $C_{1-4}$ alkane sulfonate, arene sulfonate, $C_{1-4}$ perfluoroalkanesulfonate, tetrafluoroborate, perhalogenate, sulfate, hydrogen sulfate or carboxylate,

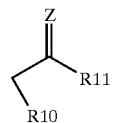
(III)

in which
- $R^{10}$ is a $C_{1-4}$ acyl group, aroyl, $C_{1-4}$ alkylsulfonyl, $C_{1-4}$ alkylsulfinyl, $C_{1-4}$ alkylamino, di-$C_{1-4}$-alkylamino, vinylcarbonyl, methineimino, nitrile, ester or carboxylic acid amide group which may optionally be substituted by $C_{1-4}$ alkyl, $C_{2-4}$ hydroxyalkyl or aryl groups and
- $R^{11}$ is a $C_{1-4}$ acyl, $C_{1-4}$ alkoxy, $C_{1-4}$ alkylamino, $C_{1-4}$ acylamino or di-$C_{1-4}$-alkylamino group,
- the substituents $R^{10}$ and $R^{11}$ together with the rest of the molecule forming a 5-, 6- or 7-membered heterocycle from the series of 1,3-thiazolidine-2,5-diones, 1,3-thiazolidine-2-thione-5-ones, perhydropyrimidine-2,4,6-triones, perhydropydmidine-2-thione-4,6-diones, cyclopentane-1,3-diones, cyclo-hexane-1,3-diones, indolines, indan-1,3-diones, indan-1-ones, 2-pyrazoline-5ones, 1,2-dihydro-6-hydroxy-2-hydroxypyridines or enol esters thereof, and
- Z represents oxygen, sulfur or the dicyanomethylene group, and/or reaction products of the compounds corresponding to formulae I and II and/or III.

DETAILED DESCRIPTION OF THE INVENTION

In the context of the invention, keratin-containing fibers are understood to include wool, pelts, feathers and, in particular, human hair. In principle, however, the colorants according to the invention may also be used to color other natural fibers such as, for example, cotton, jute, sisal, linen or silk, modified natural fibers such as, for example, regenerated cellulose, nitro, alkyl or hydroxyalkyl or acetyl cellulose and synthetic fibers such as, for example, polyamide, polyacrylonitrile, polyurethane and polyester fibers.

Preferred compounds corresponding to formula I are, for example, 4-dimethylaminobenzaldehyde, 4-diethylaminobenzaldehyde, 4-dimethyl-amino-2-hydroxybenzaldehyde, 4-pyrrolidinobenzaldehyde, 4-morpholino-benzaldehyde, 4-piperidinobenzaldehyde, 4-dimethylaminoacetophenone, 4-dimethylaminonaphthaldehyde, 4-dimethylaminobenzylidene acetone, 4-dimethylamino cinnamaldehyde, 2-dimethylaminobenzaldehyde, 2-chloro-4-dimethylaminobenzaldehyde, 4-dimethylamino-2-methylbenzaldehyde, trans-4-diethylaminocinnamaldehyde, 4-(dibutylaminoybenzaldehyde, 4-diphenylaminobenzaldehyde, 2,3,6,7-tetrahydro-1H,5H-benzo[ij]quino-ziline-9-carboxaldehyde, 4-dimethylamino-2-methoxybenzaldehyde, 2,3,6,7-tetrahydro8-hydroxy-1H, 5H-benzo[ij]quinoziline-9-carboxaldehyde, 4-(1-imidazolylbenzaldehyde, 2-morpholinobenzaldehyde, indole-3-carboxaldehyde, 1-methylindole-3-carboxaldehyde, N-ethylcarbazole-3-aldehyde, 2-formylmethylene-1,3,3-trimethylindoline (Fischer's aldehyde or tribase aldehyde) and mixtures thereof.

Examples of preferred compounds corresponding to formula II are 1,4-dimethylquinolinium, 1,2-dimethylquinolinium, 1,4-dimethylpyridinium, 1,2-dimethylpyridinium, 2-methyl-1-ethylqinolinium, 2,3-dimethylisoquinolinium, 1,2,3,3-tetramethyl-3H-indolinium, 2,3-dimethylbenzothiazolium, 2,3-dimethyl-6-nitrobenzothiazolium, 3-benzyl-2-benzothiazolium, 2-methyl-3-propyl benzothiazolium, 2,4-dimethyl-3-ethylthiazolium, 3-(2-carboxyethyl)-2,5-dimethylbenzothiazolium, 1,2,3-trimethylbenzimidazolium, 5,6-dichloro-1,3-diethyl-2-methyl benzimidazolium, 3-ethyl-2-methylbenzothiazolium, 3-ethyl-2-methylnaphtho[1,2-d]thiazolium, 5-chloro-3-ethyl-2-methylbenzothiazolium, 3-ethyl-2-methyl benzoxazolium salts which may be present, for example, as chlorides, bromides, iodides, methanesulfonates, benzenesulfonates, p-toluenesulfonates, trifluoromethane sulfonates, methyl sulfates, tetra-fluoroborates and 2-methyl-3-(3-sulfopropylbenzothiazolium hydroxide, inner salt, 5-methoxy-2-methyl-3-(3-sulfopropyl)-benzothiazolium hydroxide, inner salt and mixturesof the above.

Examples of compounds corresponding to formula III are rhodanine, rhodanine-3-acetic acid, barbituric acid, thiobarbituric acid, 1,3-dimethyl and 1,3-diethyl thiobarbituric acid, oxindole, 3-indoxyl acetate, coumaranone, 1-methyl-3-phenylpyrazolinone, indan-1,3-dione, cyclopentane-1,3-dione, 1,2-dihydro-1-ethyl-6-hydroxy-4-methyl-2-oxo-3-pyridinecarbonitrile and mixtures of the above.

Examples of reaction products of the compounds corresponding to formulae I and II and/or III are Quinaldine Red (2-[4-(dimethylamino)-styryl]-1-ethyl quinolinium iodide), 2-[4-(dimethylamino)-styryl]-1-methyl quinolinium iodide, 2-[Sdimethylamino)-styryl]-1-ethylpyridinium iodide, 2-[4-(dimethylamino)-styryl]-1-methylpyridinium iodide, 4-[4-dimethylaminostyryl]-1-methyl pyridinium tosylate, 4-[2-(2,3,6,7-tetrahydro-1H,5H-benzo[ij]quinolizin-9-yl)ethenyl]-1-methylpyridinium iodide, trans4-[4-(dibutylaminokstyryl]-1-methyl pyridinium iodide and 2,6-bis-[4-(dimethylamino)-styryl]-1-methylpyridinium iodide, 2-[4-(dimethylamino)-styryl]-3-methyl benzoxazolium perchlorate, 2-[4-(dimethylamino)-styryl]-3-methyl benzoxazolium iodide, 2-[4-(dimethylamino)-styryl-1-ethyinaphthol[1,2-d]thiazolium iodide.

These compounds are largely known from the literature or are commercially obtainable or may be obtained by known syntheses.

The above-mentioned compounds corresponding to formula I, formula II and formula III are used in the compositions according to the invention in quantities of preferably 0.03 to 65 mmol and more preferably 1 to 40 mmol, based on 100 g of the colorant as a whole. They may be used as substantive colorants or in the presence of typical oxidation dye precursors.

Colorants which contain the combination according to the invention as sole coloring component are preferably used for colors in the yellow, orange, red and violet range.

In order to obtain further and more intensive colors, the colorants according to the invention may additionally contain color intensifiers. The color intensifiers are preferably selected from the group consisting of piperidine, piperidine-2-carboxylic acid, piperidine-3-carboxylic acid, piperidinecarboxylic acid, pyridine, 2-hydroxypyridine, 3-hydroxypyridine, 4-hydroxypyridine, imidazole, 1-methyl imidazole, histidine, pyrrolidine, proline, pyrrolidone, pyrrolidone-5-carboxylic acid, pyrazole, 1,2,4-triazole, piperazidine, derivatives and physiologically compatible salts thereof.

The color intensifiers mentioned above may be used in a quantity of 0.03 to 65 and more particularly 1 to 40 mmol, based on 100 g of the colorant as a whole.

Various combinations of the compounds corresponding to formula I, II and/or III may also be used together in all colorants. Similarly, various color intensifiers may also be used together.

Oxidizing agents, for example $H_2O_2$, need not be present. However, it may be desirable in some cases to add hydrogen peroxide or other oxidizing agents to the compositions according to the invention to obtain shades which are lighter than the keratin-containing fibers to be colored. Oxidizing agents are generally used in a quantity of 0.01 to 6% by weight, based on the solution applied. A preferred oxidizing agent for human hair is $H_2O_2$.

In one preferred embodiment, the colorants according to the invention contain typical substantive dyes, for example from the group of nitrophenylenediamines, nitroaminophenols, anthraquinones or indophenols, in addition to the compounds present in accordance with the invention in order further to modify the color tones. Examples of suitable substantive dyes are the compounds known under the International names or commercial names of HC Yellow 2, HC Yellow 4, HC Yellow 6, Basic Yellow 57, Disperse Orange 3, HC Red 3, HC Red BN, Basic Red 76, HC Blue 2, Disperse Blue 3, Basic Blue 99, HC Violet 1, Disperse Violet 1, Disperse Violet 4, Disperse Black 9, Basic Brown 16 and Basic Brown 17 and also picramic acid, 2-aminochloro-4-nitrophenol, 4-amino-2-nitrodiphenylamine-2'-carboxylic acid, 6-nitro-1,2,3,4-tetrahydroquinoxaline, 4-N-ethyl-1,4-bis-(2'-hydroxyethylamino)-2-nitrobenzene hydrochloride and 1-methyl-3-nitro4-(2'-hydroxyethyl)-aminobenzene. The compositions according to the invention in this embodiment contain the substantive dyes in a quantity of, preferably, 0.01 to 20% by weight, based on the colorant as a whole.

In addition, the compositions according to the invention may also contain naturally occurring dyes such as, for example, henna red, henna neutral, henna black, camomile blossom, sandalwood, black tea, black alder bark, sage, logwood, madder root, catechu, sedre and alkanet.

Compounds I and II present in accordance with the invention or the color intensifiers and substantive dyes optionally present do not have to be single compounds. Instead, the hair colorants according to the invention—due to the processes used for producing the individual dyes—may contain small quantities of other components providing they do not adversely affect the coloring result or have to be ruled out for other reasons, for example toxicological reasons.

The colorants according to the invention produce intensive colors even at physiologically compatible temperatures of <45° C. Accordingly, they are particularly suitable for coloring human hair. For application to human hair, the colorants are normally incorporated in a water-containing cosmetic carrier. Suitable water-containing cosmetic carriers are, for example, creams, emulsions, gels or even surfactant-containing foaming solutions, for example shampoos or other formulations suitable for application to the keratin-containing fibers. If necessary, the colorants may even be incorporated in water-free carriers.

The colorants according to the invention may also contain any of the known active substances, additives and auxiliaries typical of such formulations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants.

Suitable anionic surfactants for the compositions according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether, amide groups and hydroxyl groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

linear fatty acids containing 10 to 22 carbon atoms (soaps), ether carboxylic acids corresponding to the formula R—O—$(CH_2$—$CH_2O)_x$—$CH_2$—COOH, in which R is a linear alkyl group containing 10 to 22 carbon atoms and x=0 or1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—$O(CH_2$—$CH_2O)_x$—$SO_3H$, in which R is a preferably linear alkyl group containing 10 to 18 carbon atoms and x=0 or 1 to 12, mixtures of surfaceactive hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated $C_{8-22}$ carboxylic acids, such as oleic acid, stearic acid, isostearic acid and palmitic acid.

In the context of the invention, zwitterionic surfactants are surface-active compounds which contain at least one quaternary ammonium group and at least one $—COO^{(-)}$ or $—SO_3^{(-)}$ group in the molecule. Particularly suitable zwitterionic surfactants are the so-called betaines, such as N-alkyl-N,N-dimethyl ammonium glycinates, for example coconutalkyl dimethyl ammonium glycinate, N-acylaminopropyl-N,N-dimethyl ammonium glycinates, for example coconutacylaminopropyl dimethyl ammonium glycinate, and 2-alkyl-3-carboxymethyl-3-hydroxyethyl imidazolines containing 8 to 18 carbon atoms in the alkyl or acyl group and coconutacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surfaceactive compounds which, in addition to a $C_{8-18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-coconutalkyl aminopropionate, coconutacyl aminoethyl aminopropionate and $C_{12-18}$ acyl sarcosine.

Nonionic surfactants contain, for example, a polyol group, a poly-alkylene glycol ether group or a combination of polyol and polyglycol ether groups as the hydrophilic group. Examples of such compounds are products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group, $C_{12-22}$ fatty acid monoesters and diesters of products of the addition of 1 to 30 moles of ethylene oxide onto glycerol, $C_{8-22}$ alkyl mono- and oligoglycosides and ethoxylated analogs thereof, products of the addition of 5 to 60 moles of ethylene oxide onto castor oil and hydrogenated castor oil, products of the addition of ethylene oxide onto sorbitan fatty acid esters, products of the addition of ethylene oxide onto fatty acid alkanolamides.

Examples of cationic surfactants suitable for use in the hair treatment formulations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethi-cone), Dow Corning 929 Emulsion (containing a hydroxylamino-modified silicone which is also known as amodimethicone), SM-2059 (manufacturer: General Electric), SLM-55067 (manufacturer Wacker) and Abil®-Quat 3270 and 3272 (manufacturer: Th. Goldschmidt; diquaternary polydimethyl siloxanes, quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the a methyl hydroxyalkyl dialkoyloxyalkyl ammonium methosulfates marketed under the trade name of Stepantex®, are also readily biodegradable.

One example of a quaternary sugar derivative suitable for use as a cationic surfactant is the commercially available product Glucquat® 100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

Other active substances, auxiliaries and additives are, for example, nonionic polymers such as, for example, vinyl pyrrolidone/vinyl acrylate copolymers, polyvinyl pyrrolidone and vinyl pyrrolidone/vinyl acetate copolymers and polysiloxanes, cationic polymers, such as quaternized cellulose ethers, polysiloxanes containing quaternary groups, dimethyl diallyl ammonium chloride polymers, acrylamide/ dimethyl diallyl ammonium chloride copolymers, dimethyl aminoethyl methacrylatelvinyl pyrrolidone copolymers quaternized with diethyl sulfate, vinyl pyrrolidone/imidazolinium methochloride copolymers and quatemized polyvinyl alcohol, zwitterionic and amphoteric polymers such as, for example, acrylamidopropyl/trimethyl ammonium chloridelacrylate copolymers and octyl acrylamide/methyl methacrylate/tert.butyl aminoethyl methacrylate/2-hydroxypropyl methacrylate copolymers, anionic polymers such as, for example, polyacrylic acids, crosslinked polyacrylic acids, vinyl acetate/crotonic acid copolymers, vinyl pyrrolidone/vinyl acrylate copolymers, vinyl acetatelbutyl maleatel isobomyl acrylate copolymers, methyl vinyl etherlmaleic anhydride copolymers and acrylic acid/ethyl acrylate/N-tert.butyl acrylamide terpolymers, thickeners, such as agar agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol, structurants, such as glucose and maleic acid, hair-conditioning compounds, such as phospholipids, for example soya lecithin, egg lecithin and kephalins, and also silicone oils, protein hydrolyzates, more particularly elastin, collagen, keratin, milk protein, soya protein and wheat protein hydrolyzates, condensation products thereof with fatty acids and quatemized protein hydrolyzates, perfume oils, dimethyl isosorbide and cyclodextrins, solubilizers, such as ethanol, isopropanol, ethylene glycol, propylene glycol, glycerol and diethylene glycol, antidandruff agents, such as Piroctone Olamine and Zinc Omadine, other substances for adjusting the pH value, active substances, such as panthenol, pantothenic acid, allantoin, pyrrolidone carboxylic acids and salts thereof, plant extracts and vitamins, cholesterol, UV filters, consistency factors, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates, imidazoles, tannins, pyrrole, opacifiers, such as latex, pearlizers, such as ethylene glycol mono- and distearate, propellents, such as propane/butane mixtures, $N_2O$, dimethyl ether, $CO_2$ and air and antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

It can be of advantage to the coloring result to add ammonium or metal salts to the colorants. Suitable metal salts are, for example, formates, carbonates, halides, sulfates, butyrates, valerates, caproates, acetates, lactates, glycolates, tartrates, citrates, gluconates, propionates, phosphates and phosphonates of alkali metals, such as potassium, sodium or lithium, alkaline earth metals, such as magnesium, calcium, strontium or barium, or of aluminium, manganese, iron, cobalt, copper or zinc, sodium acetate, lithium bromide, calcium bromide, calcium gluconate, zinc chloride, zinc sulfate, magnesium chloride, magnesium sulfate, ammonium carbonate, chloride and acetate being preferred. These salts are preferably present in a quantity of 0.03 to 65 mmol and more preferably in a quantity of 1 to 40 mmol, based on 100 g of the colorant as a whole.

The pH value of the ready-to-use coloring compositions is normally in the range from 2 to 12 and preferably in the range from 4 to 10.

The present invention also relates to the use of a combination of aromatic aldehydes or ketones corresponding to formula I:

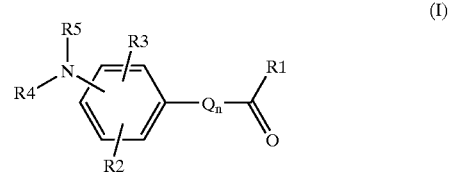

(I)

in which $R^1$ is a hydrogen atom, a $C_{1-4}$ alkyl or an aryl group, $R^2$ and $R^3$ independently of one another represent a hydrogen atom, a $C_{1-4}$ alkyl group, a halogen atom, a hydroxy, $C_{1-4}$ alkoxy or nitro group or together form a fused aromatic ring, $R^4$ and $R^5$ represent a hydrogen atom, a $C_{1-4}$ alkyl, $C_{2-4}$ hydroxyalkyl, $C_{1-4}$ alkenyl or aryl group or, together with the nitrogen atom, form a five- to seven-membered heterocyclic ring or one of them forms a saturated or unsaturated 5-, 6- or 7-membered ring with one of the substituents $R^2$ or $R^3$, Q is a direct bond or a vinylene or vinylidene group which, together with one of the two substituents $R^4$ or $R^5$, may form an indole ring or—where an exocydic double bond is formed—an indoline ring and n=1 or 2, and CH-active compounds corresponding to formulae II and/or III:

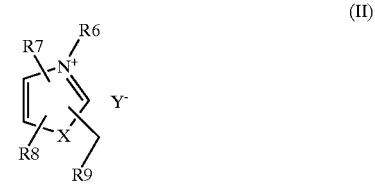

(II)

in which $R^6$ is a $C_{1-10}$ alkyl, $C_{2-10}$ alkenyl, $C_{2-4}$ hydroxyalkyl, $C_{2-4}$ carboxyalkyl, $C_{2-4}$ sulfoalkyl or aralkyl group, $R^7$ and $R^8$ independently of one another represent a hydrogen atom, a $C_{1-4}$ alkyl group, a halogen atom, a hydroxy, $C_{1-4}$ alkoxy or nitro group or together form a fused aromatic ring, $R^9$ represents a hydrogen atom, a $C_{1-4}$ alkyl or an aryl group, X is an oxygen or sulfur atom, the group >N-$R^{12}$ or —CH=CH—, where $R^{12}$ is a $C_{1-4}$ alkyl, $C_{2-4}$ carboxyalkyl, $C_{2-4}$ sulfoalkyl, $C_{2-4}$ sulfoxyalkyl, $C_{2-4}$ hydroxyalkyl or aralkyl group, and $Y^-$ is an anion selected from halide, $C_{1-4}$ alkyl sulfate, $C_{1-4}$ alkane sulfonate, arene sulfonate, $C_{1-4}$ perfluoroalkanesulfonate, tetrafluoroborate, perhalogenate, sulfate, hydrogen sulfate or carboxylate,

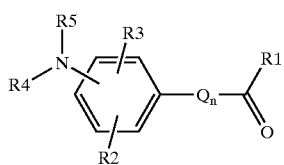

(III)

in which $R^{10}$ is a $C_{1-4}$ acyl group, aroyl, $C_{1-4}$ alkylsulfonyl, $C_{1-4}$ alkylsulfinyl, $C_{1-4}$ alkylamino, di-$C_{1-4}$-alkylamino, vinylcarbonyl, methineimino, nitrile, ester or carboxylic acid amide group which may optionally be substituted by $C_{1-4}$ alkyl, $C_{2-4}$ hydroxyalkyl or aryl groups and $R^{11}$ is a $C_{1-4}$ acyl, $C_{1-4}$ alkoxy, $C_{1-4}$ alkylamino, $C_{1-4}$ acylamino or di-$C_{1-4}$-alkylamino group, the substituents $R^{10}$ and $R^{11}$ together with the rest of the molecule forming a 5-, 6- or 7-membered heterocycle from the series of 1,3-thiazolidine-2,5-diones, 1,3-thiazolidine-2-thione-5-ones, perhydropyrimidine-2,4,6-triones, perhydropyrimidine-2-thione-4,6-diones, cyclopentane-1,3-diones, cyclo-hexane-1,3-diones, indolines, indan-1,3-diones, indan-1-ones, 2-pyrazoline-5-ones, 1,2-dihydro-6-hydroxy-2-hydroxypyridines or enol esters thereof, and Z represents oxygen, sulfur or the dicyanomethylene group, and/or reaction products of these compounds, as a coloring component in oxidation hair colorants.

The present invention also relates to a process for coloring keratin-containing fibers, more particularly human hair, in which a colorant containing a combination of aromatic aldehyde or ketones corresponding to formula I:

(I)

in which $R^1$ is a hydrogen atom, a $C_{1-4}$ alkyl or an aryl group, $R^2$ and $R^3$ independently of one another represent a hydrogen atom, a $C_{1-4}$ alkyl group, a halogen atom, a hydroxy, $C_{1-4}$ alkoxy or nitro group or together form a fused aromatic ring, $R^4$ and $R^5$ represent a hydrogen atom, a $C_{1-4}$ alkyl, $C_{2-4}$ hydroxyalkyl, $C_{1-4}$ alkenyl or aryl group or, together with the nitrogen atom, form a five- to seven-membered heterocyclic ring or one of them forms a saturated or unsaturated 5-, 6- or 7-membered ring with one of the substituents $R^2$ or $R^3$, Q is a direct bond or a vinylene or vinylidene group which, together with one of the two substituents $R^4$ or $R^5$, may form an indole ring or—where an exocyclic double bond is formed—an indoline ring and n=1 or 2, and CH-active compounds corresponding to formulae II and/or III:

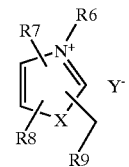

(II)

in which $R^6$ is a $C_{1-10}$ alkyl, $C_{2-10}$ alkenyl, $C_{2-4}$ hydroxyalkyl, $C_{2-4}$ carboxyalkyl, $C_{2-4}$ sulfoalkyl or aralkyl group, $R^7$ and $R^8$ independently of one another represent a hydrogen atom, a $C_{1-4}$ alkyl group, a halogen atom, a hydroxy, $C_{1-4}$ alkoxy or nitro group or together form a fused aromatic ring, $R^9$ represents a hydrogen atom, a $C_{1-4}$ alkyl or an aryl group, X is an oxygen or sulfur atom, the group >N-$R^{12}$ or —CH=CH—, where $R^{12}$ is a $C_{1-4}$ alkyl, $C_{2-4}$ carboxyalkyl, $C_{2-4}$ sulfoalkyl, $C_{2-4}$ sulfoxyalkyl, $C_{2-4}$ hydroxyalkyl or aralkyl group, and $Y^-$ is an anion selected from halide, $C_{1-4}$ alkyl sulfate, $C_{1-4}$ alkane sulfonate, arene sulfonate, $C_{1-4}$ perfluoroalkanesulfonate, tetrafluoroborate, perhalogenate, sulfate, hydrogen sulfate or carboxylate,

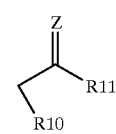

(III)

in which $R^{10}$ is a $C_{1-4}$ acyl group, aroyl, $C_{1-4}$ alkylsulfonyl, $C_{1-4}$ alkylsulfinyl, $C_{1-4}$ alkylamino, di-$C_{1-4}$-alkylamino, vinylcarbonyl, methineimino, nitrile, ester or carboxylic acid amide group which may optionally be substituted by $C_{1-4}$ alkyl, $C_{2-4}$ hydroxyalkyl or aryl groups and $R^{11}$ is a $C_{1-4}$ acyl, $C_{1-4}$ alkoxy, $C_{1-4}$ alkylamino, $C_{1-4}$ acylamino or di-$C_{1-4}$-alkylamino group, the substituents $R^{10}$ and $R^{11}$ together with the rest of the molecule forming a 5-, 6- or 7-membered heterocycle from the series of 1,3-thiazolidine-2,5-diones, 1,3-thiazolidine-2-thionee-5-ones, perhydropyrimidine-2,4,6-triones, perhydropyrimidine-2-thione 4,6-diones, cyclopentane-1,3-diones, cyclo-hexane-1,3-diones, indolines, indan-1,3-diones, indan-1-ones, 2-pyrazoline-5-ones, 1,2-dihydro-6-hydroxy-2-hydroxypyridines or enol esters thereof, and Z represents oxygen, sulfur or the dicyanomethylene group, and/or reaction products of these compounds and typical cosmetic ingredients is applied to the keratin-containing fibers, left thereon for a while, usually about 30 minutes, and then rinsed out or washed out with a shampoo.

The aromatic aldehydes or ketones corresponding to formula I and the CH-active compounds corresponding to formula II and/or III may be applied to the hair either simultaneously or successively; in the latter case, it does not matter which of the two components is applied first. The ammonium or metal salts optionally present may be added to the first component or to the secondcomponent. A period of up to 30 minutes may elapse between application of the first component and the second component. The fibers may also be pretreated with the salt solution.

The aromatic aldehydes or ketones corresponding to formula I and the CH-active compounds corresponding to formulae II and/or III may be stored either separately or together either in a liquid or paste-form preparation (water-based or water-free) or as a dry powder. In the event of separate storage, the components are thoroughly mixed together just before application. In the event of dry storage, a certain quantity of warm (30 to 80° C.) water is normally added and a homogeneous mixture prepared before application.

EXAMPLES

Preparation of a Coloring Solution

Suspensions of 5 mmol of an aromatic aldehyde or ketone corresponding to formula I and 5 mmol of a CH-active compound corresponding to formula II or III in 25 ml of water at 60° C. were prepared. After cooling to 30° C., the suspensions were mixed together, 5 mmol of sodium acetate, optionally 5 mmol of piperidine and one drop of a 20% fatty alkyl ether sulfate solution were added and the pH was adjusted accordingly with dilute NaOH or hydrochloric acid.

Where reaction products of the compounds of formula I and A compounds of formula II or III were used, 5 mmol of the reaction product a was suspended or dissolved in 50 ml of water.

A tress of 90% grey, non-pretreated human hair was placed in this coloring solution for 30 minutes at 30° C. The tress was then rinsed for 30 seconds with luke-warm water, dried with warm air and then combed out.

The particular shades and depths of color are shown in the following Tables.

The depth of color was evaluated on the following scale:

| | |
|---|---|
| − | very faint, if any, color |
| (+) | weak intensity |
| + | medium intensity |
| +(+) | medium to strong intensity |
| ++ | strong intensity |
| ++(+) | strong to very strong intensity |
| +++ | very strong intensity |

TABLE 1

| Aromatic aldehyde or ketone | Compound of formula II or III | Color intensifier | pH | Color | Intensity |
|---|---|---|---|---|---|
| 4-Dimethylamino-benzaldehyde | 1-Ethyl-2-methyl quinolinium iodide | Piperidine | 9.0 | Violet-red | ++(+) |
| 4-Dimethylamino-benzaldehyde | 1,4-Dimethyl quinolinium methane sulfonate | Piperidine | 9.0 | Red-violet | +(+) |
| 4-Dimethylamino-benzaldehyde | 3-Ethyl-2-methylbenzo-thiazolium-p-toluene-sulfonate | Piperidine | 7.60 | Bright pinky red | +++ |
| 4-Dimethylamino-benzaldehyde | Rhodanine | Piperidine | 7.60 | Bright orange | ++(+) |
| 4-Dimethylamino-benzaldehyde | Oxindole | Piperidine | 9.00 | Gold-yellow | ++(+) |
| 4-Dimethylamino-benzaldehyde | 1,3-Diethylthiobarbituric acid | — | 9.00 | Orange | ++ |
| 4-Dimethylamino-benzaldehyde | 1-Ethyl-2-methylnaphtho-[1,2-d]-thiazolium-p-toluenesulfonate | — | 6.00 | Carmine red | ++(+) |
| 4-Dimethylamino-1-naphthaldehyde | 1-Ethyl-2-methylnaphtho-[1,2-d]-thiazolium-p-toluenesulfonate | — | 6.00 | Dark violet | ++(+) |
| 4-Dimethylamino-1-naphthaldehyde | 3-Ethyl-2-methylbenzothia-zolium-p-toluenesulfonate | Piperidine | 7.73 | Red violet | ++(+) |
| 4-Dimethylamino-1-naphthaldehyde | 1-Ethyl-2-methyl quinolinium iodide | Piperidine | 9.00 | Violet-brown | +(+) |
| 4-Dimethylamino-cinnamaldehyde | 1-Ethyl-2-methyl quinolinium iodide | Piperidine | 9.00 | Dark orange-brown | ++(+) |
| 4-Dimethylamino-cinnamaldehyde | 3-Ethyl-2-methylbenzothia-zolium-p-toluenesulfonate | Piperidine | 7.33 | Brown | ++ |
| 4-Dimethylamino-cinnamaldehyde | Rhodanine | — | 6.00 | Red-orange | ++ |
| 4-Dimethylamino-cinnamaldehyde | Rhodanine acetic acid | — | 6.00 | Orange-red | ++(+) |
| 4-Dimethylamino-cinnamaldehyde | 1,3-Diethyl thiobarbituric acid | — | 9.00 | Brown-violet | ++ |
| 4-Dimethylamino-cinnamaldehyde | 1,4-Dimethyl quinolinium methane sulfonate | Piperidine | 9.00 | Dark yellow-brown | ++ |
| 1,3,3-Trimethyl-2-for-mylmethylene indoline | 1,4-Dimethylquinolinium methanesulfonate | Piperidine | 9.00 | Grey-green | + |

TABLE 1-continued

| Aromatic aldehyde or ketone | Compound of formula II or III | Color intensifier | pH | Color | Intensity |
|---|---|---|---|---|---|
| (tribase aldehyde) | | | | | |
| Tribase aldehyde | 3-Ethyl-2-methylbenzoxazolium iodide | — | 6.00 | Pinky red | + |
| Tribase aldehyde | 3-Ethyl-2-methylbenzoxazolium iodide | Piperidine | 9.00 | Dark pinky red | ++(+) |
| Tribase aldehyde | 3-Ethyl-2-methylbenzothiazolium-p-toluenesulfonate | Piperidine | 8.50 | Pinky red (pink) | ++ |
| Tribase aldehyde | 3-Ethyl-2-methylnaphtho[1,2-d]-thiazolium-p-toluenesulfonate | — | 7.27 | Violet-orange | + |
| 1-Methylindole-3-aldehyde | 1-Ethyl-2-methylnaphtho[1,2-d]-thiazolium-p-toluenesulfonate | — | 6.00 | Red-orange | ++(+) |
| Indole-3-aldehyde | 1-Ethyl-2-methylnaphtho[1,2-d]-thiazolium-p-toluenesulfonate | — | 6.00 | Yellow-orange | + |
| Indole-3-aldehyde | 3-Ethyl-2-methylbenzothiazolium iodide | — | 6.00 | Gold-yellow | + |

TABLE 2

Coloring with reaction products of compounds I and II

| Reaction product | Color | Intensity | pH |
|---|---|---|---|
| 2-(4-Dimethylaminostyryl)-1-ethylpyridinium iodide | Bright orange | +++ | 6.00 |
| 2-(4-Dimethylaminostyryl)-1-methyl quinolinium iodide | Violet-red | ++(+) | 6.00 |
| 4-[(1-methyl-4(1H)-pyridinylidene]-ethylidene-2,5-cyclohexadien-1-one | Orange-yellow | +(+) | 6.00 |
| 3-(4-Dimethylaminobenzylidene)-2-indolinone | Gold-yellow | ++ | 6.00 |
| 5-(4-Dimethylaminobenzylidene)-5-thioxo-2-pyrrolidinone | Bright orange | ++ | 6.00 |
| 2-(4-Dimethylaminostyryl)-3-ethyl benzothiazolium iodide | Bright orange | ++ | 6.00 |

What is claimed is:

1. A composition for coloring keratin-containing fibers comprising a mixture of, or a reaction product of, or both of:

(A) at least one aromatic aldehyde or ketone corresponding to formula I:

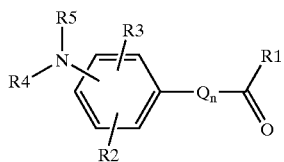

(I)

wherein $R^1$ represents a hydrogen atom, a $C_{1-4}$ alkyl group or an aryl group, wherein $R^2$ and $R^3$, independently of one another, represent a hydrogen atom, a $C_{1-4}$ alkyl group, a halogen atom, a hydroxy group, a $C_{1-4}$ alkoxy group or a nitro group, or $R^2$ and $R^3$ together form a fused aromatic ring, wherein $R^4$ and $R^5$, independently of one another, represent a hydrogen atom, a $C_{1-4}$ alkyl group, a $C_{2-4}$ hydroxyalkyl group, a $C_{1-4}$ alkenyl group or aryl group, or $R^4$ and $R^5$ together with the nitrogen atom form a five- to seven-membered heterocyclic ring, or one of $R^4$ or $R^5$ forms a saturated or unsaturated 5-, 6- or 7-membered ring with one of the substituents $R^2$ or $R^3$, wherein Q is a direct bond, a vinylene group or vinylidene group, wherein the vinylene group or vinylidene group may optionally together with one of the two substituents $R^4$ or $R^5$, form an indole ring or an indoline ring, and wherein n is 1 or 2; and (B) one or more CH-active compounds corresponding to formula II, formula III, or mixtures thereof:

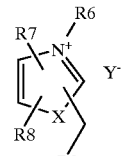

(II)

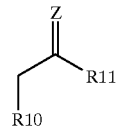

(III)

wherein $R^6$ represents a $C_{1-10}$ alkyl group, a $C_{2-10}$ alkenyl group, a $C_{2-4}$ hydroxyalkyl group, a $C_{2-4}$ carboxyalkyl group, a $C_{2-4}$ sulfoalkyl group or an aralkyl group, wherein $R^7$ and $R^8$, independently of one another, represent a hydrogen atom, a $C_{1-4}$ alkyl group, a halogen atom, a hydroxy group, a $C_{1-4}$ alkoxy group or a nitro group, or $R^7$ and $R^8$ together form a fused aromatic ring, wherein $R^9$ represents a hydrogen atom, a $C_{1-4}$ alkyl group or an aryl group, wherein X is an oxygen atom or sulfur atom, a >N-$R^{12}$ group or —CH=CH— group, where $R^{12}$ is a $C_{1-4}$ alkyl group, a $C_{2-4}$ carboxyalkyl group, a $C_{2-4}$ sulfoalkyl group, a $C_{2-4}$ sulfoxyalkyl group, a $C_{2-4}$ hydroxyalkyl group or an aralkyl group, wherein $Y^-$ represents an anion selected from a halide, a $C_{1-4}$ alkyl sulfate, a $C_{1-4}$ alkane sulfonate, an arene sulfonate, a $C_{1-4}$ perfluoroalkanesulfonate, a tetrafluoroborate, a perhalogenate, a sulfate, a hydrogen sulfate or a carboxylate, wherein $R^{10}$ represents a $C_{1-4}$ acyl group, an aroyl group, a $C_{1-4}$ alkylsulfonyl group, a $C_{1-4}$ alkylsulfinyl group, a $C_{1-4}$ alkylamino group, a di-$C_{1-4}$-alkylamino group, a vinylcarbonyl group, a methineimino group, a nitrile group, an ester or a carboxylic acid amide group, the carboxylic acid amnide group being optionally substituted by one or more $C_{1-4}$ alkyl, $C_{2-4}$ hydroxyalkyl or aryl groups, wherein $R^{11}$ represents a $C_{1-4}$ acyl group, a $C_{1-4}$ alkoxy group, a $C_{1-4}$ alkylamino group, a $C_{1-4}$ acylamino group or a di-$C_{1-4}$-alkylamino group, or wherein the substituents $R^{10}$ and $R^{11}$ together with the rest of the molecule form a 5-, 6- or 7-membered heterocycle selected from 1,3-thiazolidine-2,5-done, 1,3-thiazolidine-2-thione-5-one, perhydropyridine-2,4,6-trione, perhydropyrimidine-2-thione-4,6-dione, cyclopentane-1,3-dione, cyclohexane-1,3-dione, indole, indan-1,3-dione, indan-1-one, 2-pyrazoline-5-one, 1,2-dihydro-6-hydroxy-2-hydroxypyridine or an enol ester derivative of the 5- to 7-membered heterocycle, and wherein Z represents oxygen, sulfir or a dicyanomethylene group.

2. The composition of claim 1 wherein the aromatic aldehyde or ketone of formula I comprises a compound selected from 4-dimethylaminobenzaldehyde, 4-diethylaminobenzaldehyde, 4-dimethylamino-2-hydroxybenzaldehyde, 4-pyrrolidinobenzaldehyde, 4-morpholinobenzaldehyde, 4-piperidinobenzaldehyde, 4-diethylaminoacetophenone, 4-dimethylaminonaphthaldehyde, 4-dimethylaminobenzylidene acetone, 4-dimethylamino cinnamaldehyde, 2-dimethylaminobenzaldehyde, 2-chloro-4-dimethylaminobenzaldehyde, 4-dimethylamino-2-methylbenzaldehyde, trans-4-diethylaminocinnamaldehyde, 4-(dibutylamino)-benzaldehyde, 4-diphenylaminobenzaldehyde, 2,3,6,7-tetrahydro-1H,5H-benzo[ij]quinoziline-9-carboxaldehyde, 4-dimethylamino-2-methoxybenzaldehyde, 2,3,6,7-tetrahydro-8-hydroxy-1H,5H-benzo[ij]quinoziline-9carboxaldehyde, 4-(1-imidazolyl)-benzaldehyde, 2-morpholinobenzaldehyde, indole-3-carboxaldehyde, 1-methylindole-3-carboxaldehyde, N-ethylcarbazole-3-aldehyde, 2-formylmethylene-1,3,3-trimethylindoline or mixtures thereof.

3. The composition of claim 1, wherein the composition comprises a compound corresponding to formula II selected from a salt of 1,4-dimethylquinolinium, 1,2-dimethylquinolinium, 1,4-dimethylpyridinium, 1,2-dimethylpyridinium, 2-methyl-1-ethylqinolinium, 2,3-dimethylisoquinolinium, 1,2,3,3-tetramethyl-3H-indoliniun, 2,3-dimethylbenzothiazolium, 2,3-dimethyl-6-nitrobenzothiazolium, 3-benzyl-2-benzothiazolium, 2-methyl-3-propyl benzothiazolium, 2,4-dimethyl-3-ethylthiazolium, 3-(2-carboxyethyl)-2.5-dimethylbenzothiazolium, 1,2,3-trimethylbenzimidazolium, 5,6-dichloro-1,3-diethyl-2-methyl benzimidazolium, 3-ethyl-2-methylbenzothiazolium, 3-ethyl-2-methylnaphtho[1,2-d]thiazolium, 5-chloro-3-ethyl-2-methylbenzothiazolium, or 3-ethyl-2-methyl benzoxazolium, or 2-methyl-3-(3-sulfopropyl)-benzothiazolium hydroxide or an inner salt thereof, or 5-methoxy-2-methyl-3-(3-sulfopropyl)-benzo-thiazolium hydroxide or an inner salt thereof, or mixtures of any of the foregoing compounds corresponding to formula II.

4. The composition of claim 3 wherein $Y^-$ of the salt comprises one or more chlorides, bromides, iodides, methanesulfonates, benzenesulfonates, p-toluenesulfonates, trifluoromethane sulfonates, methyl sulfates, tetrafluoroborates, or mixtures thereof.

5. The composition of claim 1, wherein the composition comprises a compound corresponding to formula III selected from rhodanine, rhodanine-3-acetic acid, barbituric acid, thiobarbituric acid, 1,3-dimethyl thiobarbituric acid, 1,3-diethyl thiobarbituric acid, oxindole, 3-indoxyl acetate, coumaranone, 1-methyl-3-phenylpyrazolinone, indan-1,3-dione, cyclopentane-1,3-dione, 1,2-dihydro-1-ethyl-6-hydroxy 4-methyl-2-oxo-3-pyridinecarbonitrile or mixtures thereof.

6. The composition of claim 1 wherein the composition comprises a reaction of the aromatic aldehyde or ketone of formula I and the CH-active compound, and the reaction product is selected from Quinaldine Red (2-[4-(dimethylamino)-styryl]-1-ethyl quinolinium iodide), 2-[4-(dimethylamino)-styryl]-1-methyl quinolinium iodide, 2-[4-(dimethylamino)-styryl]-1-ethylpyridinium iodide, 2-[4-(dimethylamino)-styryl]-1-methylpyridinium iodide, 4-[4-dimethylaminostyryl]-1-methyl pyridinium tosylate, 4-[2-(2,3,6,7-tetrahydro-1H,5H-benzo[ij]quinolizin-9-yl)-ethenyl]-1-methylpyridinium iodide, trans-4-[4-(dibutylamino)-styryl]-1-methyl pyridinium iodide, 2,6-bis-[4-(dimethylamino)styryl]-1-methylpyridinium iodide, 2-[4-(dimethylamino)-styryl]-3-methyl benzoxazolium perchlorate, 2-[4-(dimethylamino)-styryl]-3-methyl benzoxazolium iodide, or 2-[4-(dimethylamino)-styryl-1-ethylnaphthol[1,2-d]thiazolium iodide or mixtures thereof.

7. The composition of claim 1, wherein the aromatic aldehyde or ketone corresponding to formula I and the compound of formula II or formula III are each present in the composition in an amount of 0.03 mmol to 65 mmol, based on 100 grams of the composition as a whole.

8. The composition of claim 7, wherein the aromatic aldehyde or ketone corresponding to formula I and the compound of formula II or formula III are each present in the composition in an amount of 1 mmol to 40 mmol, based on 100 grams of the composition as a whole.

9. The composition of claim 1, further comprising one or more color intensifiers selected from piperidine, piperidine-2-carboxylic acid, piperidine-3-carboxylic acid, piperidine4-carboxylic acid, pyridine, 2-hydroxypyridine, 3-hydroxypyridine, 4-hydroxypyridine, imidazole, 1-methyl imidazole, histidine, pyrrolidine, proline, pyrrolidone, pyrrolidone-5-carboxylic acid, pyrazole, 1,2,4-triazole or piperazidine, or mixtures thereof.

10. The composition of claim 1 further comprising from 0.01 weight percent to 20 weight percent, based on the total weight of the composition, of one or more substantive dyes selected from nitrophenylenediamines, nitroaminophenols, anthraquinones or indophenols, or combinations thereof.

11. The composition of claim 1 further comprising one or more ammonium or metal salts selected from formates, carbonates, halides, sulfates, butyrates, valerates, caproates, acetates, lactates, glycolates, tartrates, citrates, gluconates, propionates, phosphates or phosphonates or combinations thereof.

12. The composition of claim 11 wherein the cationic component of the ammonium or metal salts comprises one or more ammonium ions, alkali metals, alkaline earth metals, aluminum, manganese, iron, cobalt, copper or zinc or mixtures thereof.

13. The composition of claim 1 further comprising one or more oxidizing agents.

14. The composition of claim 13 wherein the oxidizing agents comprise from 0.01 weight percent to 6 weight percent $H_2O_2$, based on the total weight of the composition.

15. The composition of claim 1, further comprising one or more anionic, zwitterionic or nonionic surfactants, or combinations thereof.

16. A process for coloring keratinontaining fibers comprising applying to keratin containing fibers (a) at least one aromatic aldehyde or ketone corresponding to formula I:

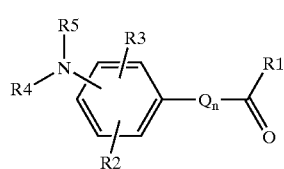
(I)

wherein $R^1$ represents a hydrogen atom, a $C_{1-4}$ alkyl group or an aryl group, wherein $R^2$ and $R^3$ independently of one another, represent a hydrogen atom, a $C_{1-4}$ alkyl group, a halogen atom, a hydroxy group, a $C_{1-4}$ alkoxy group or a nitro group, or $R^2$ and $R^3$ together form a fused aromatic ring, wherein $R^4$ and $R_5$, independently of one another, represent a hydrogen atom, a $C_{1-4}$ alkyl group, a $C_{2-4}$ hydroxyalkyl group, a $C_{1-4}$ alkenyl group or aryl group, or $R^4$ and $R^5$ together with the nitrogen atom form a five- to seven-membered heterocyclic ring, or one of $R^4$ or $R^5$ forms a saturated or unsaturated 5-, 6- or 7-membered ring with one of the substituents $R^2$ or $R^3$, wherein Q is a direct bond, a vinylene group or vinylidene group, wherein the vinylene group or vinylidene group may optionally together with one of the two substituents $R^4$ or $R^5$, form an indole ring or an indoline ring, and wherein n is 1 or 2; and (b) one or more CH-active compounds corresponding to formula II, formula III or mixtures thereof:

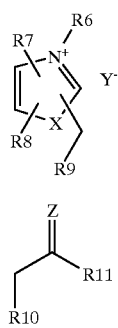

wherein $R^6$ represents a $C_{1-10}$ alkyl group, a $C_{2-10}$ alkenyl group, a $C_{2-4}$ hydroxyalkyl group, a $C_{2-4}$ carboxyalkyl group, a $C_{2-4}$ sulfoalkyl group or an aralkyl group, wherein $R^7$ and $R^8$, independently of one another, represent a hydrogen atom, a $C_{1-4}$ alkyl group, a halogen atom, a hydroxy group, a $C_{1-4}$ alkoxy group or a nitro group, or $R^7$ and $R^8$ together form a fused aromatic ring, wherein $R^9$ represents a hydrogen atom, a $C_{1-4}$ alkyl group or an aryl group, wherein X is an oxygen atom or sulfur atom, a >N-$R^{12}$ group or —CH=CH— group, where $R^{12}$ is a $C_{1-4}$ alkyl group, a $C_{2-4}$ carboxyalkyl group, a $C_{2-4}$ sulfoalkyl group, a $C_{2-4}$ sulfoxyalkyl group, a $C_{2-4}$ hydroxyalkyl group or an aralkyl group, wherein $Y^-$ represents an anion selected from a halide, a $C_{1-4}$ alkyl sulfate, a $C_{1-4}$ alkane sulfonate, an arene sulfonate, a $C_{1-4}$ perfluoroalkanesulfonate, a tetrafluoroborate, a perhalogenate, a sulfate, a hydrogen sulfate or a carboxylate, wherein $R^{10}$ represents a $C_{1-4}$ acyl group, an aroyl group, a $C_{1-4}$ alkylsulfonyl group, a $C_{1-4}$ alkylsulfinyl group, a $C_{1-4}$ alkylamino group, a di-$C_{1-4}$-alkylamino group, a vinylcarbonyl group, a methineimino group, a nitrile group, an ester or a carboxylic acid amide group, the carboxylic acid amide group being optionally substituted by one or more $C_{1-4}$ alkyl, $C_{2-4}$ hydroxyalkyl or aryl groups, wherein $R^{11}$ represents a $C_{1-4}$ acyl group, a $C_{1-4}$ alkoxy group, a $C_{1-4}$ alkylamino group, a $C_{1-4}$ acylamino group or a di-$C_{1-4}$-alkylamino group, or wherein the substituents $R^{10}$ and $R^{11}$ together with the rest of the molecule form a 5-, 6- or 7-membered heterocycle selected from 1,3-thiazolidine-2,5-dione, 1,3-thiazolidine-2-thione-5-one, perhydropyrimidine-2,4,6-trione, perhydropyrimidine-2-thione-4,6-dione, cyclopentane-1,3-dione, cyclohexane-1,3-dione, indole, indan-1,3-dione, indan-1-one, 2-pyrazoline-5-one, 1,2-dihydro-6-hydroxy-2-hydroxypyridine or an enol ester derivative of the 5- to 7-membered heterocycle, and wherein Z represents oxygen, sulfuir or a dicyanomethylene group.

17. The method of claim 16 wherein the aromatic aldehyde or ketone of formula I and the CH-active compound are applied simultaneously or successively in any order to the keratin-containing fibers.

18. The method of claim 16 wherein the aromatic aldehyde or ketone and the CH-active compound are formulated into a coloring composition prior to the applying step.

19. The method of claim 16 wherein the coloring composition comprises a reaction product of the aromatic aldehyde or ketone and the CH-active compound.

20. The method of claim 16 wherein the keratin-containing fiber is hair, and following the applying step, the aromatic aldehyde or ketone and the CH-active compound are washed out with a shampoo or rinsed out from the hair after a ontact time of about 30 minutes.

* * * * *

UNITED STATES PATENT AND TRADEMARK OFFICE
CERTIFICATE OF CORRECTION

PATENT NO. : 6,770,102 B1
DATED : August 3, 2004
INVENTOR(S) : Moeller et al.

It is certified that error appears in the above-identified patent and that said Letters Patent is hereby corrected as shown below:

Column 15,
Line 67, delete "vinylidcne" and insert -- vinylidene --.

Column 17,
Line 1, delete "amnide" and insert -- amide --.
Line 8, delete "1,3-thiazolidine-2,5-done" and insert -- 1,3-thiazolidine-2,5-dione --.
Lines 9 through 10, delete "perhydropyridine-2,4,6-trione" and insert
-- perhydropyrimidine-2,4,6-trione --.
Line 16, delete "sulfir" and insert -- sulfur --.
Line 24, delete "4-diethylaminoacetophenone" and insert -- 4-dimethylaminoacetophenone --.

Column 18,
Line 37, delete "piperidine4-carboxylic" and insert -- piperidine-4-carboxylic --.
Line 66, delete "keratinontaining" and insert -- keratin-containing --.

Column 19,
Line 14, add a comma after "$R^3$".
Line 19, delete "$R_5$" and insert -- $R^5$ --.

Column 20,
Line 53, delete "ontact" and insert -- contact --.

Signed and Sealed this

Seventh Day of December, 2004

JON W. DUDAS
*Director of the United States Patent and Trademark Office*